(12) United States Patent
Perschbacher

(10) Patent No.: US 8,185,200 B2
(45) Date of Patent: May 22, 2012

(54) DISABLE FOR ATRIOVENTRICULAR DELAY ADJUSTMENT

(75) Inventor: David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 748 days.

(21) Appl. No.: 12/325,952

(22) Filed: Dec. 1, 2008

(65) Prior Publication Data

US 2009/0143833 A1    Jun. 4, 2009

Related U.S. Application Data

(60) Provisional application No. 61/005,504, filed on Dec. 4, 2007.

(51) Int. Cl.
*A61N 1/365* (2006.01)
(52) U.S. Cl. .............................................. 607/14; 607/9
(58) Field of Classification Search .................. 607/4, 5, 607/9, 14, 15, 25
See application file for complete search history.

(56) References Cited

U.S. PATENT DOCUMENTS

| | | | |
|---|---|---|---|
| 4,712,556 A | 12/1987 | Baker, Jr. | |
| 4,860,749 A | 8/1989 | Lehmann | |
| 4,944,298 A | 7/1990 | Sholder | |
| 5,653,738 A | 8/1997 | Sholder | |
| 5,893,882 A | 4/1999 | Peterson et al. | |
| 6,128,533 A | 10/2000 | Florio et al. | |
| 6,233,485 B1 * | 5/2001 | Armstrong et al. | 607/14 |
| 6,411,847 B1 | 6/2002 | Mower | |
| 6,484,058 B1 | 11/2002 | Williams et al. | |
| 7,376,461 B2 | 5/2008 | Perschbacher et al. | |
| 2001/0014817 A1 | 8/2001 | Armstrong et al. | |
| 2004/0077963 A1 | 4/2004 | Perschbacher et al. | |

FOREIGN PATENT DOCUMENTS

| | | |
|---|---|---|
| EP | 1923098 A2 | 5/2008 |
| WO | WO-00/78390 A1 | 12/2000 |
| WO | WO-2009/073159 A1 | 6/2009 |

OTHER PUBLICATIONS

"U.S. Appl. No. 10/274,697, Interview Summary mailed Oct. 10, 2007", 2 pgs.
"U.S. Appl. No. 10/274,697, Interview Summary mailed Oct. 18, 2007", 2 pgs.

(Continued)

*Primary Examiner* — Niketa Patel
*Assistant Examiner* — Rex R Holmes
(74) *Attorney, Agent, or Firm* — Schwegman, Lundberg & Woessner, P.A.

(57) ABSTRACT

An apparatus comprises an electrical stimulation circuit, a ventricular sensing circuit, a ventricular sensing timer, and an atrial pacing timer. The ventricular sensing circuit detects an intrinsic ventricular tachyarrhythmia depolarization. The ventricular sensing timer initiates timing of a lowest tachy rate (LTR) zone interval and also a ventricular pace interval that is calculated using a lower rate limit (LRL). The atrial pacing timer calculates an atrial pace interval to follow the intrinsic ventricular depolarization using the ventricular pace interval less a paced atrioventricular (AV) delay interval, delays generation of the atrial pace until after expiration of the LTR zone interval by decreasing the paced AV delay interval when the calculated atrial pace interval is within the LTR zone interval, and disables decreasing of the paced AV delay interval when the LRL interval less the paced AV delay interval at the LRL is less than the LTR zone interval.

20 Claims, 3 Drawing Sheets

OTHER PUBLICATIONS

"U.S. Appl. No. 10/274,697, Interview Summary mailed Dec. 20, 2005", 4 pgs.

"U.S. Appl. No. 10/274,697, Amendment and Response filed Mar. 8, 2007 to Final Office Action mailed Jul. 11, 2006", 7 pgs.

"U.S. Appl. No. 10/274,697, Amendment and Response filed May 15, 2006 to Non-Final Office Action mailed Jan. 19, 2006", 6 pgs.

"U.S. Appl. No. 10/274,697, Amendment and Response filed Oct. 18, 2005 to Non-Final Office Action mailed Sep. 14, 2005", 9 pgs.

"U.S. Appl. No. 10/274,697, Amendment and Response filed Dec. 16, 2005 to Final Office Action mailed Nov. 17, 2005", 5 pgs.

"U.S. Appl. No. 10/274,697, Final Office Action mailed Jul. 11, 2006", 6 pgs.

"U.S. Appl. No. 10/274,697, Final Office Action mailed Nov. 17, 2005", 7 pgs.

"U.S. Appl. No. 10/274,697, Non-Final Office Action mailed Jan. 19, 2006", 4 pgs.

"U.S. Appl. No. 10/274,697, Non-Final Office Action mailed Jul. 9, 2007", 5 pgs.

"U.S. Appl. No. 10/274,697, Non-Final Office Action mailed Sep. 14, 2005", 8 pgs.

"U.S. Appl. No. 10/274,697, Notice of Allowance mailed Jan. 23, 2008", 4 pgs.

"U.S. Appl. No. 10/274,697, Response filed Nov. 8, 2007 to Non-Final Office Action mailed Jul. 9, 2007", 10 pgs.

"International Application Serial No. PCT/US2008/013247, International Search Report mailed Mar. 27, 2009", 4 pgs.

"International Application Serial No. PCT/US2008/013247, Written Opinion mailed Mar. 27, 2009", 8 pgs.

* cited by examiner

DISABLE FOR ATRIOVENTRICULAR DELAY ADJUSTMENT

CLAIM OF PRIORITY

This non-provisional application claims the benefit of priority under 35 U.S.C. §119(e) to U.S. Provisional Patent Application Ser. No. 61/005,504, filed Dec. 4, 2007, the specification of which is herein incorporated by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. Such devices can include pacers, defibrillators, cardioverters, cardiac resynchronization therapy (CRT), or various combinations of such devices. Such devices can typically sense intrinsic heart contractions, deliver pacing pulses to evoke responsive heart contractions, or deliver a shock to interrupt certain arrhythmias. This can help improve the patient's heart rhythm or can help coordinate a spatial nature of the heart contraction, either of which may improve cardiac output of blood to help meet the patient's metabolic need for such cardiac output.

For example, detecting a ventricular tachyarrhythmia (e.g., a too-fast ventricular heart rhythm) often involves detecting a rate of ventricular heart contractions that exceeds a tachyarrhythmia rate threshold. By using multiple tachyarrhythmia rate thresholds, multiple tachyarrhythmia rate zones can be established, which can further classify different tachyarrhythmias based on which zone the heart rate falls within.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
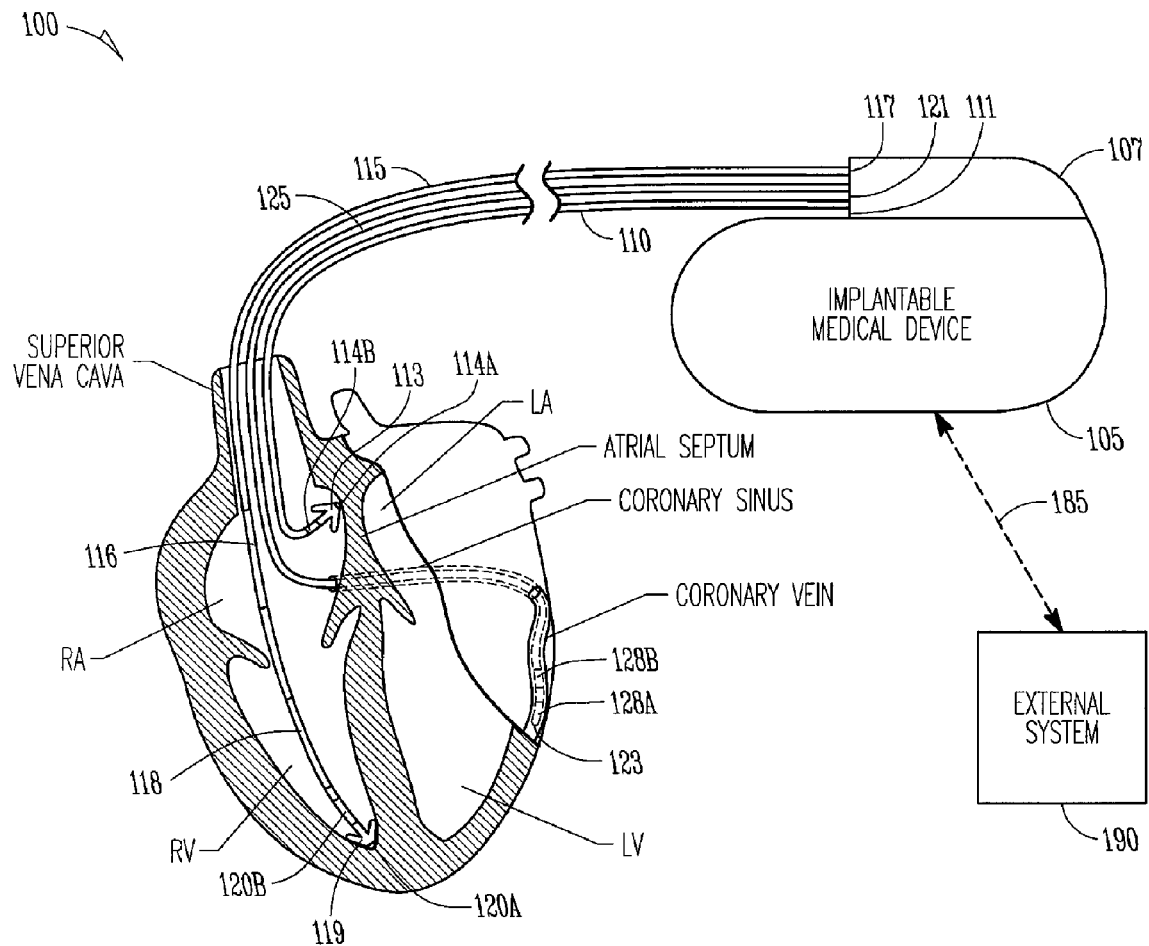
FIG. 1 is an illustration of portions of a system that uses an implantable medical device.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As set forth above, tachyarrhythmia rate zones can be established, which can classify different tachyarrhythmias based on a zone the heart rate falls within. However, when an atrial pace is delivered at a heart rate that falls within a tachyarrhythmia rate zone, such a "fast" atrial pace can inhibit detection of a tachyarrhythmic intrinsic ventricular contraction that occurs close in time to the fast atrial pace. This, in turn, can prevent proper diagnosis or treatment of a ventricular tachyarrhythmia.

Figure 2:
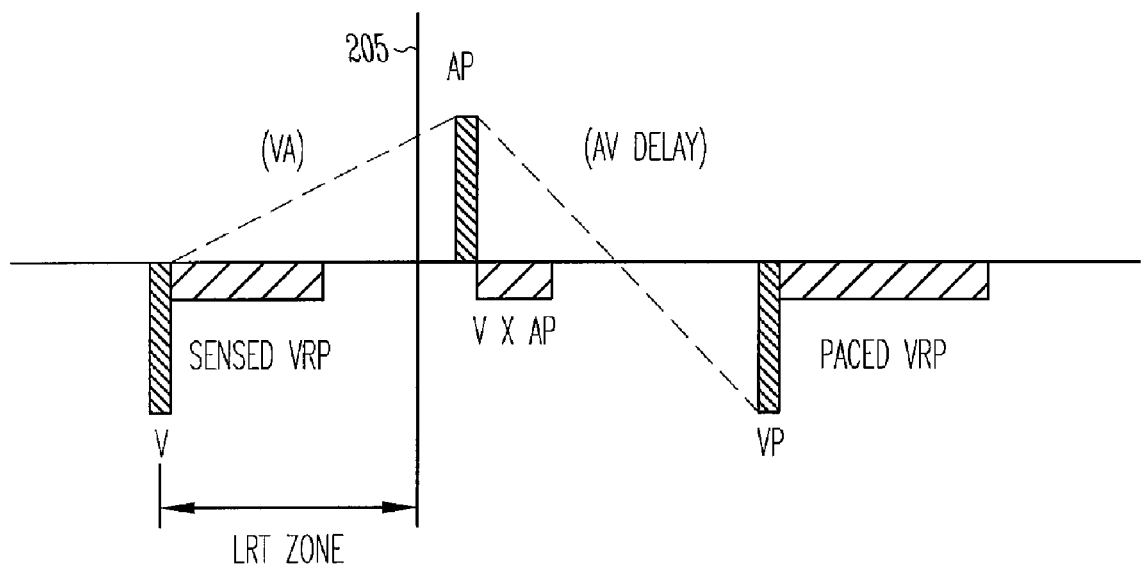
FIG. 2 is an example of a timing diagram illustrating a manner in which timing cycles are set up in a multi-chamber pacemaker or pacemaker/defibrillator.

FIG. 2 is an example of a timing diagram illustrating a manner in which timing cycles are set up in a multi-chamber pacemaker or pacemaker/defibrillator. Starting with an intrinsic Ventricular beat (V) a time is established when ventricular pace (VP) electrical stimulation energy will be delivered by the pacemaker. In some examples this ventricular pace pulse interval is determined by programmable variables including the "maximum tracking rate" MTR and the "down-rate smooth limit" (drs). These two factors are multiplied to determine the ventricular pace pulse interval. For example, with a MTR of 500 and a drs of 1.12, the time interval from the sensed beat V to the next paced beat (VP) would be 560 milliseconds. FIG. 2 shows that there is a ventricular refractory period (VRP) associated with the intrinsic sensed event V and with the pace event VP.

In some examples this ventricular pace pulse interval is determined using an established lower rate limit (LRL) interval. The LRL interval can be a programmable variable, or the LRL interval can be determined from a programmable LRL. VP occurs when the LRL interval times out.

The atrioventricular (AV) delay value may be a parameter programmed in by the physician or can be a dynamic value calculated by the pacemaker. If the AV delay is dynamic a minimum AV delay may be specified in the IMD. The dynamic AV delay interval is not allowed to decrease below this specified value to preserve a minimum delay between an atrial pace and a ventricular pace.

The AV delay establishes the time of occurrence of the A-pace (AP) pulse produced by the implantable device. A paced AV delay is subtracted from the ventricular pace pulse interval to determine the ventricular-atrial (VA delay) and the AP time.

FIG. 2 also shows that following the AP signal, a preprogrammed A-pace cross-channel refractory period is provided (V×AP). Finally, FIG. 2 shows a vertical line 205 to represent an interval to define a lowest tachyarrhythmia, or lowest tachy, rate (LRT) zone interval. Tachyarrhythmia is sometimes categorized into three rate zones—VF, VT, and VT-1. Zone VF is for ventricular fibrillation and is the highest rate zone. Zone VT is for ventricular tachycardia. Zone VT-1 is sometimes referred to as slow tachy. A programmed interval referred to as the "lowest tachy zone interval" defines the lower boundary of the VT-1 rate zone. It is the longest interval (slowest rate) that sensed beats can have and be classified as a tachycardia. This parameter varies from patient-to-patient and is arrived at by observing ECG data for the patient over a period of time.

Figure 3:
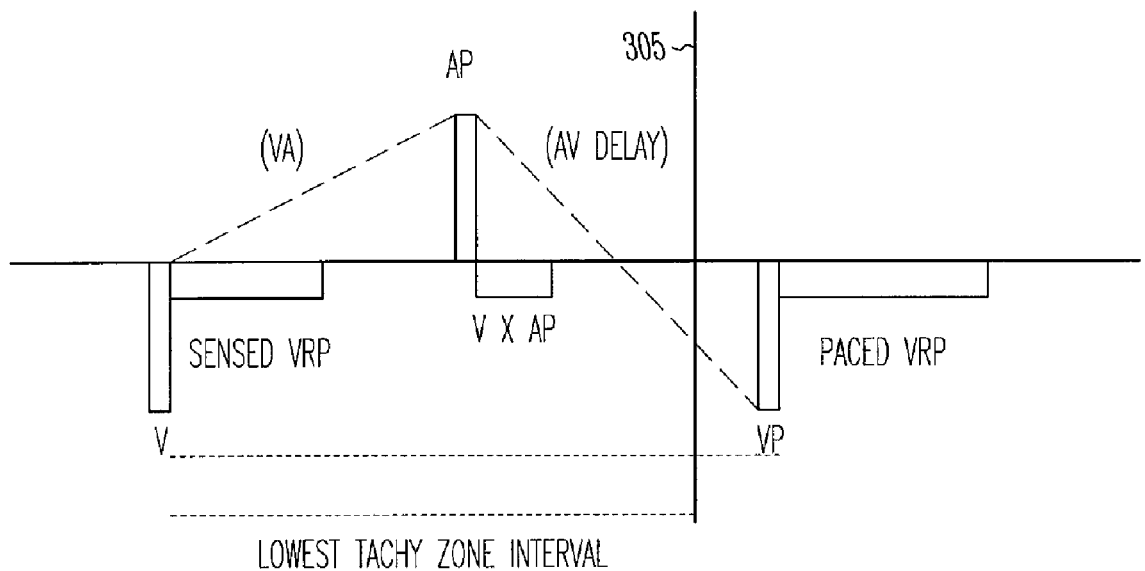
FIG. 3 is another example of a timing diagram illustrating a manner in which timing cycles are set up in a multi-chamber pacemaker or pacemaker/defibrillator.

FIG. 3 is another example of a timing diagram illustrating a manner in which timing cycles can be set up in a multi-chamber pacer or pacer/defibrillator. In this example, the determined VP pulse interval is less than the VP pulse interval in FIG. 2. In the example of FIG. 3, the calculated AP time is within the LTR zone interval indicated by the vertical line 305. An intrinsic ventricular event that occurs within the LTR zone can be possibly indicative of a tachyarrhythmia episode. The interval between the occurrence of the atrial pace (AP) and the vertical line 305 can be a zone in which under-sensing can occur. This can be due to the atrial cross-channel refractory period that follows the AP pulse. The atrial cross-channel refractory period that follows the AP pulse can inhibit sensing of an intrinsic ventricular event that occurs during the atrial cross-channel refractory period. This under-sensing can be avoided if the AV delay is decreased (or "squeezed") so that the calculated AP occurs outside the LTR zone.

Figure 4:
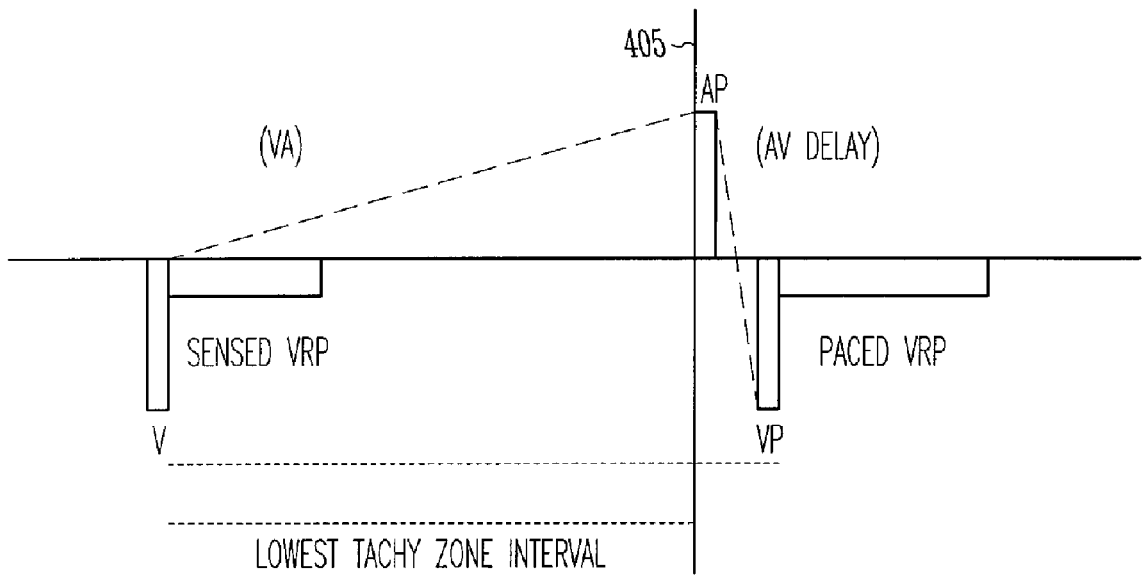
FIG. 4 is an example of a timing diagram illustrating avoiding under-sensing by decreasing an AV delay.

An example of this is shown in the timing diagram example of FIG. 4. In the example of FIG. 4, the AV delay is reduced enough such that the AP pulse occurs outside the LTR zone interval shown by the vertical line 405. Note that in this example the VP pacing interval is preserved. In some cases, a physician or other user may set the LRL to a high value (or conversely, may set the LRL interval to a small value). For example, a short LRL may be desirable for pediatric patients, along with a corresponding shortened AV delay interval. This LRL AV delay may be programmed by the physician or other user, or may be calculated by the implantable device using the LRL interval. If the LRL interval is short enough (e.g., approaching the LTR zone interval) the calculated AP pulse may fall within the LTR zone interval. If the AV squeeze were not disabled, the device may move the AP pulse outside the LTR zone, potentially defeating the LRL interval desired by the physician. For this reason, if the LRL interval is programmed short enough so that it approaches the LTR zone interval, the "AV squeeze" that automatically decreases the AV delay to cause the AP to fall outside the LTR zone interval can be automatically disabled. Stated in equation form, if $$(\text{LTR zone Interval}) > [(\text{LRL Interval}) - (\text{AV Delay at the LRL})], \quad (1)$$

then the "AV squeeze" that automatically decreases the AV delay to cause the AP to fall outside the LTR zone is automatically disabled and the device will function using the short LRL interval and corresponding LRL AV delay desired by the physician. In some examples, the implantable device communicates a warning to an external system to indicate that the "AV squeeze" has been disabled.

Figure 5:
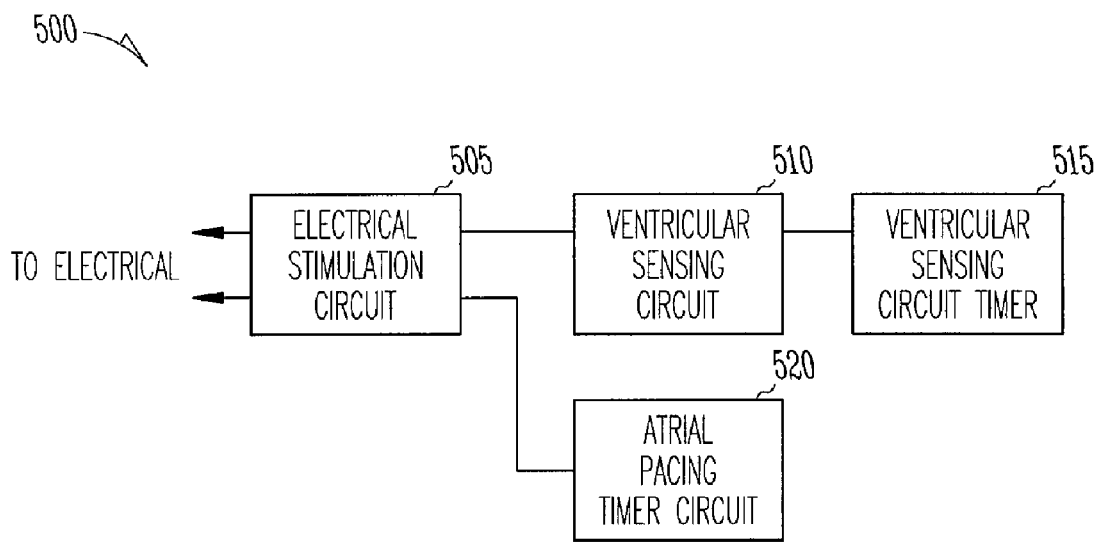
FIG. 5 is a block diagram of portions of a device that adjusts an AV delay to avoid under-sensing of tachyarrhythmia.

FIG. 5 is a block diagram of portions of a device 500 that adjusts an AV delay to avoid under-sensing of tachyarrhythmia. The device 500 includes an electrical stimulation circuit 505. The electrical stimulation circuit 505 provides pacing electrical stimulation energy to an implantable ventricular electrode and an implantable atrial electrode. The device 500 also includes a ventricular sensing circuit 510 and a ventricular sensing circuit timer 515. The ventricular sensing circuit 510 detects intrinsic ventricular depolarizations including ventricular tachyarrhythmia depolarizations. The ventricular sensing circuit timer 515 initiates timing of the LTR zone interval and also initiates timing of the VP pulse interval. In some examples, the ventricular pace pulse interval is calculated using an established LRL interval.

The device 500 further includes an atrial pacing timer circuit 520. The atrial pacing timer circuit 520 calculates the AP pulse interval to follow the intrinsic ventricular depolarization using the ventricular pace pulse interval less a paced AV delay interval. If the calculated AP pulse interval is within the LTR zone interval, the atrial pacing timer circuit 520 delays generation of the AP pulse until after expiration of the LTR zone interval by decreasing the paced AV delay interval. As shown in FIG. 4, this "AV squeeze" moves the AP pulse to outside the LTR zone while preserving the ventricular pace pulse interval. If the LRL interval less the paced AV delay interval at the LRL is less than the LTR zone interval, the atrial pacing timer circuit 520 disables the "AV squeeze" decreasing of the paced AV delay interval. Thus, in the case where the LRL is set to a high rate (e.g. near the LTR zone) and the AV delay interval is already shortened, the "AV squeeze" feature, which automatically decreases the AV delay, is disabled.

In some examples, the device 500 includes a communication circuit to communicate with an external system. Because disabling the "AV squeeze" feature may result in under-sensing of ventricular tachyarrhythmia, the device communicates an indication to the external system that the "AV squeeze" feature is disabled. The external device communicates an alert to the physician, such as by using a display of the external system.

In some examples, the external system determines from its monitoring of the therapy parameter settings of the implantable device that the "AV squeeze" feature that automatically decreases the AV delay is disabled. For example, if the external system knows the LTR zone Interval, LRL Interval, and the AV Delay at the LRL, settings of the implantable device, the external system can use Equation (1) to deduce the feature is disabled. The external device then communicates the alert to the physician.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
  an implantable medical device (IMD) comprising:
    an electrical stimulation circuit, configured to provide pacing electrical stimulation energy to an implantable ventricular electrode and an implantable atrial electrode;
    a ventricular sensing circuit, configured to detect an intrinsic ventricular tachyarrhythmia depolarization;
    a ventricular sensing circuit timer, configured to initiate timing of a lowest tachy rate (LTR) zone interval and also a ventricular pace pulse interval; and
    an atrial pacing timer circuit configured to:
      calculate an atrial pace pulse interval to follow the intrinsic ventricular depolarization using the ventricular pace pulse interval less a paced atrioventricular (AV) delay interval;

delay generation of the atrial pace pulse until after expiration of the LTR zone interval by decreasing the paced AV delay interval when the calculated atrial pace pulse interval is within the LTR zone interval, thereby preserving the ventricular pace pulse interval; and disable decreasing of the paced AV delay interval when an established lower rate limit (LRL) interval less the paced AV delay interval at the LRL interval is less than the LTR zone interval.

2. The system of claim 1, wherein the IMD includes a communication circuit communicatively coupled to the atrial pacing timer circuit, wherein the atrial pacing timer circuit is configured to communicate an alert from the IMD to another device when disabling the decreasing of the paced AV delay interval.

3. The system of claim 1,
wherein the IMD includes a communication circuit communicatively coupled to the atrial pacing timer circuit, and wherein the system includes an external device configured to:
communicate information with the IMD;
determine the LTR zone interval and the LRL interval established in the IMD;
determine the paced AV delay at the established LRL interval;
calculate the LRL interval less the paced AV delay interval at the LRL interval using the external device; and
provide an alert to a user of the external device when the LRL interval less the paced AV delay interval at the LRL interval is less than the LTR zone interval, wherein the alert indicates that the decreasing of the paced AV delay interval is disabled.

4. The system of claim 3, wherein the IMD is configured to communicate the LTR zone interval and the LRL interval with the external device.

5. The system of claim 3, wherein the external device is configured to receive the LTR zone interval and the LRL interval via a user interface.

6. The system of claim 1, wherein the IMD is configured to establish the LTR zone interval using a ventricular tachycardia detection zone.

7. The system of claim 1, wherein the IMD is configured to establish the LTR zone interval using a slow tachycardia detection zone.

8. The system of claim 1, wherein the IMD is configured to calculate the ventricular pace pulse interval using the LRL interval.

9. The system of claim 1, wherein the IMD is configured to calculate the ventricular pace pulse interval using a maximum tracking rate and a down rate smoothing limit.

10. The system of claim 1, wherein the IMD is configured to deliver one or both of electrical cardioversion therapy and electrical defibrillation therapy.

11. A method comprising:
sensing an intrinsic ventricular depolarization that falls within a lowest tachyarrhythmia rate (LTR) zone using an implantable medical device (IMD);
calculating an atrial pace pulse interval to follow the intrinsic ventricular depolarization using a ventricular pace pulse interval less a paced atrioventricular (AV) delay interval;
delaying generation of the atrial pace pulse until after expiration of an LTR zone interval by decreasing the paced AV delay interval when the calculated atrial pace pulse interval is within the LTR zone interval, thereby preserving the ventricular pace pulse interval; and
disabling the decreasing of the paced AV delay interval when an established lower rate limit (LRL) interval less the paced AV delay interval at the LRL interval is less than the LTR zone interval.

12. The method of claim 11, including communicating an alert from the IMD to an external device when disabling the decreasing of the paced AV delay interval.

13. The method of claim 11, including:
determining the LTR zone interval and the LRL interval established in the IMD using an external device;
determining the paced AV delay at the established LRL interval;
calculating the LRL interval less the paced AV delay interval at the LRL interval using the external device; and
providing an alert to a user of the external device when the LRL interval less the paced AV delay interval at the LRL interval is less than the LTR zone interval, wherein the alert indicates that the decreasing of the paced AV delay interval is disabled.

14. The method of claim 13, wherein determining the LTR zone interval and the LRL interval includes communicating the LTR zone interval and the LRL interval with the IMD.

15. The method of claim 13, wherein determining the LTR zone interval and the LRL interval includes receiving the LTR zone interval and the LRL interval into the external device via a user interface.

16. The method of claim 11, including establishing the LTR zone interval in the IMD using a ventricular tachycardia detection zone.

17. The method of claim 11, including establishing the LTR zone interval in the IMD using a slow tachycardia detection zone.

18. The method of claim 11, including calculating the ventricular pace pulse interval using the LRL interval.

19. The method of claim 11, including calculating the ventricular pace pulse interval using a maximum tracking rate and down rate smoothing limit.

20. The method of claim 11, wherein sensing an intrinsic ventricular depolarization includes sensing an intrinsic ventricular depolarization using an IMD that delivers one or both of electrical cardioversion therapy and electrical defibrillation therapy.

* * * * *